United States Patent [19]

Gurvich

[11] Patent Number: 5,994,900
[45] Date of Patent: Nov. 30, 1999

[54] TEST PHANTOM FOR INFORMATION SYSTEMS AND METHOD OF ITS USE

[76] Inventor: Victor A. Gurvich, P.O. Box 26302, 91262 Jerusalem, Israel

[21] Appl. No.: 08/395,473

[22] Filed: Feb. 28, 1995

[30] Foreign Application Priority Data

Mar. 21, 1994 [IL] Israel .......................................... 109063

[51] Int. Cl.⁶ ..................................................... G01V 3/00
[52] U.S. Cl. ............................................ 324/300; 324/321
[58] Field of Search .................................. 324/300, 306, 324/307, 309, 318, 321

[56] References Cited

U.S. PATENT DOCUMENTS

| | | | |
|---|---|---|---|
| 4,551,678 | 11/1985 | Morgan et al. | 324/321 |
| 4,613,819 | 9/1986 | Chui | 324/300 |
| 4,625,168 | 11/1986 | Meyer et al. | 324/300 |
| 4,644,276 | 2/1987 | Sierocuk et al. | 324/300 |
| 4,816,762 | 3/1989 | Bohning | 324/300 |
| 4,888,555 | 12/1989 | Vaughan et al. | 324/318 |

Primary Examiner—Louis Arana

[57] ABSTRACT

The invention relates to devices for testing and evaluation of characteristics of information and recognizing systems in particular imaging systems. It may be used for testing of medical and industrial diagnostic systems.

The test phantom for information systems is divided into several areas, being identified on the output image or on the informative field of the system. The areas are united in one or several groups. Each of groups comprises identical test elements, thereby their maximum quantity is less than the number of said areas included in the group. All of these test elements are identical within one group, but they can be different in various groups. The disposition of test elements may be changed so that their final positions are not known to the examiner but may be determined, and they are arranged so that none of said areas may contain more than one test element.

Design of test phantom and the identification of areas on the image of phantom can be executed by various ways. Each test element can be disposed in a flat disc and moved relatively to a plate divided into numbered areas, or located eccentrically in a separated disc which can be displaced within appropriate group of identified areas independently from other ones.

The operative statistical method of using test phantom provide the opportunity to obtain probabilities of true, true-positive and true-negative answers of operator.

9 Claims, 2 Drawing Sheets

TEST PHANTOM FOR INFORMATION SYSTEMS AND METHOD OF ITS USE

BACKGROUND OF THE INVENTION

The invention relates to devices for testing and evaluation of characteristics of information and recognizing systems in particular imaging systems. It may be used with efficiency for testing of medical and industrial diagnostic systems, e.g., estimating their detectability of defects and pathological details. The invention is suitable for X-ray, gamma and ultrasound diagnostic systems as well as for computer tomography and magnetic resonance imaging.

At present many of phantoms for quality control of medical and industry diagnostic systems are known (booklets of RMI, Inc., Nuclear Associates, Inc., PTW-Freiburg, Inc.; Phantoms and Computational Model in Therapy, Diagnostics and Protection—ICRU Report 48 June 1992; Test Phantoms and Optimization in Diagnostic Radiology and Nuclear Medicine—Proceedings of Discussion Workshop held in Wurzburg, Germany 15–17 June, 1992).

Most of these phantoms have definitely disposed test elements simulating defects or pathologies. The diagnostic system is evaluated by distinguishing various test elements on the output image of the system and by defining the minimum detectable size of the test element.

The main shortcoming of known phantom is the fixed position of test elements that is known to the examiner beforehand. The impossibility of impartial testing leads often to conflicting opinions between producers and users of diagnostic equipment. RMI's Low Contrast Resolution Test Tool, Model 151 or Contrast Resolution Tissue-equivalent Ultrasound Test Object (U.S. Pat. No. 4,331,021) can serve as examples of such phantoms. There are also test phantoms with changeable position of test elements (Inventor's certificate of USSR No 699915). However the lack of identification of phantom areas on the output image, which determinate coordinates of each distinguished element does not make it possible to obtain probabilities of true, true-positive and false-positive answers of the examiner. Thus it is also impossible to obtain an impartial quantitative assessment of detectability of phantom details.

SUMMARY OF THE INVENTION

The aim of the invention is to improve objectivity and accuracy of examining characteristics of information systems. The said aim is reached by the following combination of properties.

The test phantom for information systems is divided into several areas, being identified on the output image or on the informative field of the system. The areas are united in one or several groups. Each of groups comprises identical test elements, thereby their maximum quantity is less than the number of said areas included in the group. All of these test elements are identical within one group, but they can be different in various groups. The disposition of test elements may be changed so that their final positions are not known to the examiner but may be determined, and they are arranged so that none of said areas may contain more than one test element.

The identification of areas on the image of phantom can be executed:
 by special marks or objects disposed in or on the phantom; visually from the shape of the phantom, by test element disposition and/or experiment conditions; by a separate device taking part in forming the image or the information field of the system.

Each test element can be located eccentrically in a separated disc which can be displaced within appropriate group of identified areas independently from other ones.

Test elements can be disposed in a flat disc and moved relatively to a plate divided into identified areas. This will lead to the change of positions of all test elements relatively to said areas.

The test phantom can consist also of separate objects including identical test elements.

The operative and simple statistical method of using test phantom consists in obtaining an image of the phantom, choosing a group of areas, estimating the subjective likelihood of the signal's existing from test elements on the information field of system (in percentage) and the defining probabilities of examiner answer by formulas:

probability of true-positive answer $$P(Y/s) = \frac{A}{100m}; \quad (1)$$

probability of false-positive answer $$P(Y/n) = \frac{Z}{100(l-n)}; \quad (2)$$

probability of true answer $$P = 0.5 \times \left(\frac{A}{100m} - \frac{Z}{100(l-m)}\right) + 0.5, \quad (3)$$

where l is the common number of test phantom areas in the selected group being identified on the information field of system, m is the number of test elements in the checked group, A is the sum of the examiner's estimations corresponding to areas with test elements, Z is the remaining sum of the examiner's estimations.

BRIEF DESCRIPTION OF THE DRAWINGS

The novel features of the invention are set forth in the appended claims. The invention itself, however, as well as preferred mode of use and advantages thereof, will best be understood by reference to the following detailed description of an illustrative embodiment when read in conjunction with the accompanying drawings, wherein:

DESCRIPTION OF THE PREFERRED EMBODIMENT

Figure 1:
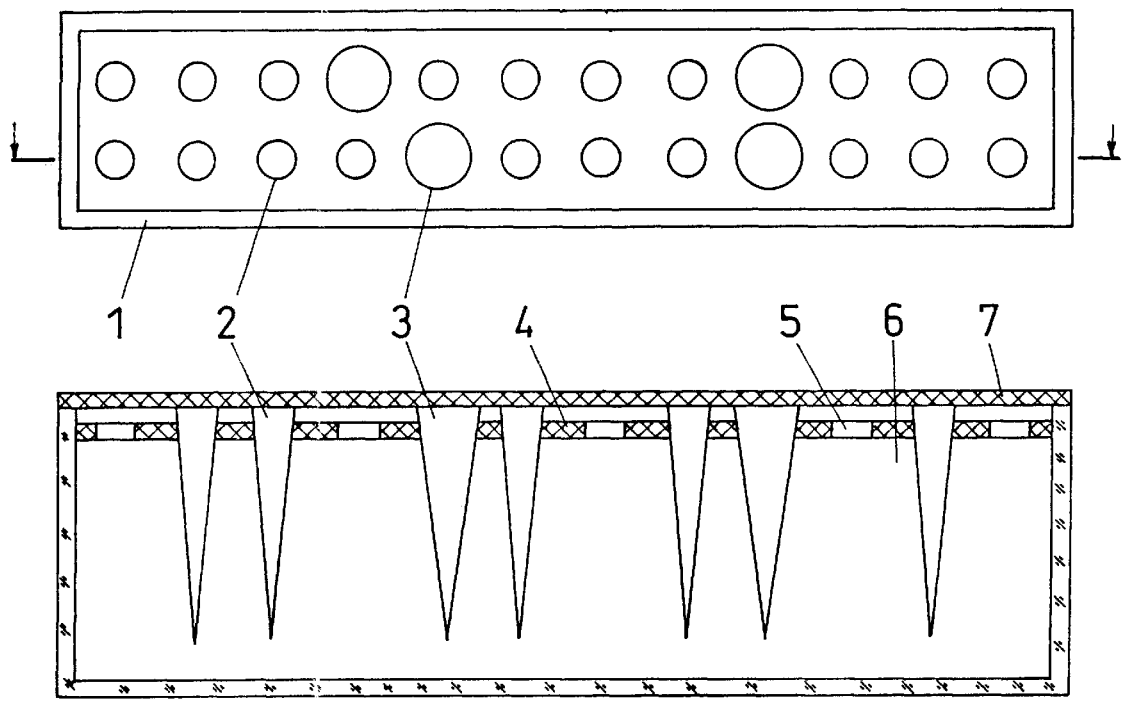
FIG. 1 is a draft of test phantom intended for examination of systems for ultrasound diagnostics, computer tomography or magnetic resonance imaging.

FIG. 1 shows one of the test phantom designs intended for control of scanning systems for ultrasound diagnostics, computer tomography or magnetic resonance imaging. The prototype of this construction is the Contrast/Detail Ultrasound Phantom described in U.S. Pat. No 4,331,021. Phantom consists of a block 1 comprising a row of conical targets. The block made of material the properties of which are identical to the material of the research object and depend on the kind of diagnostics employed. Unlike the phantom according to the U.S. Pat. No. 4,331,021 this one has one or more group of identical test elements (targets) 2 which may be displaced. For identification of phantom areas on the output image there are several measuring scales 3 made of monofilament nylon (for ultrasound) or other materials. The depth of the obtained layer is defined according to the sizes of cross section of these scales obtained during the scan. The design of the test phantom shown on FIG. 1 has a plate 4 with sockets 5, where targets can be embedded. The block 1 contains tissue equivalent gel 6. Lid 7 hermetically closes the internal space of the block 1. There are two groups of targets made from different materials shown on FIG. 1. On the output image these groups and the place of each target are distinguished by means of the certain disposition of measuring scales in the phantom.

Figure 2:
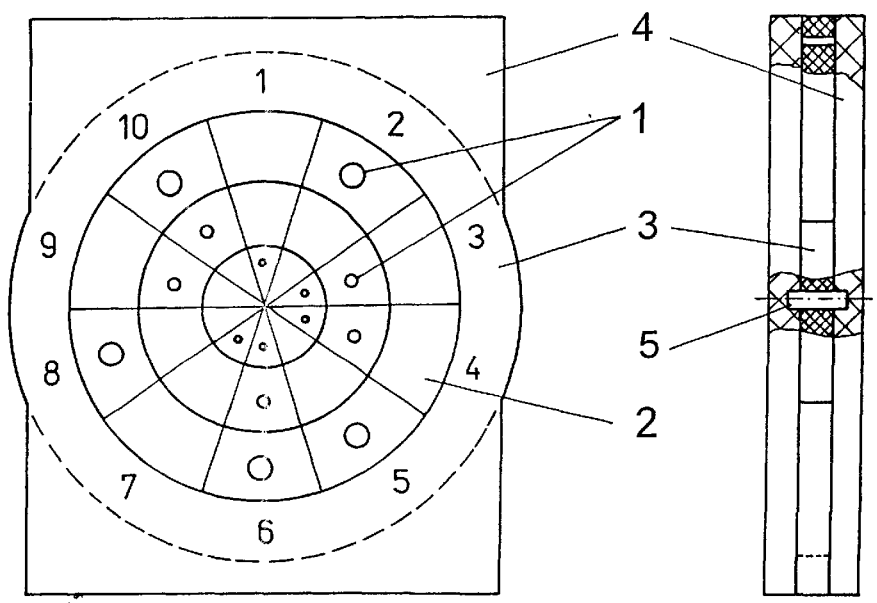
FIG. 2 is a draft of test phantom for X-ray television systems examination.

FIG. 2 shows a test phantom for X-ray television systems examination. The test phantom has a disk 3 with test elements (holes) 1 and a plate 4 divided by X-ray contrast material into several numbered sectors 2 and rings. The test elements 1 are identical within one ring but can be different in various rings. The dispositions of all the test elements 1 are changed relative to sectors 2 when a disc 3 is revolved relative to a plate 4. The disk 3 is made from a research object material and has the same axis 5 as the plate 4. Rotation of the disc 3 leads to the change of positions of each test element relative to sectors 2.

Figure 3:
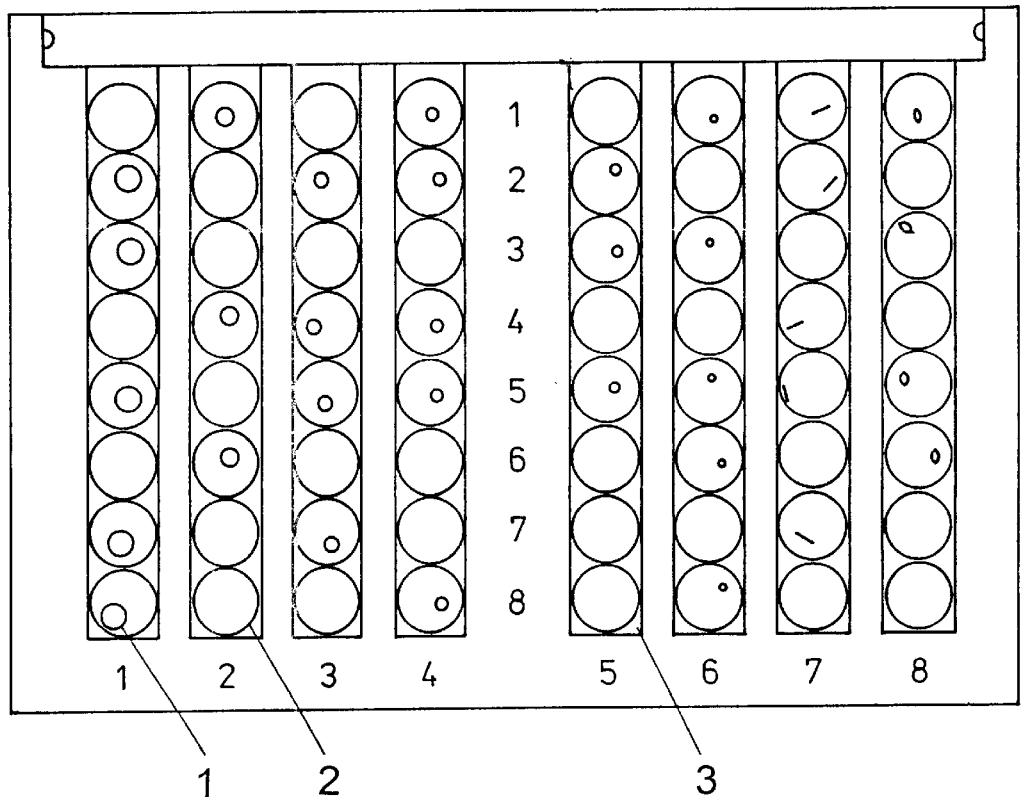
FIG. 3 is a draft of test phantom for checking radiography systems.

FIG. 3 shows a test phantom for checking radiography systems. Test elements 1 are eccentricly located in discs 2, which can be displaced within sockets 3 numbered with X-ray contrast material. Each disc 2 contains no more than one test element and can be displaced independently from other ones. The image of the disc 2 is the same while it is revolved but eccentricly located test element move. Thus, a checked area and hence reliability and accuracy of the examination increase.

Figure 4:
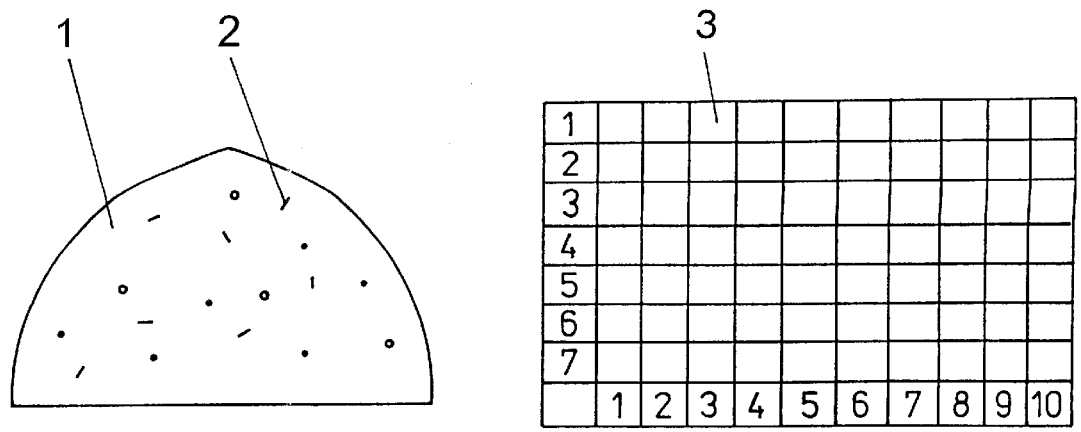
FIG. 4 is a draft of test phantom with areas being identified by a separate device which takes part in forming the output image of the system.

FIG. 4 shows a test-phantom 1 comprising simulators of defects or pathologies 2 and divided into areas by a separate plate 3 which is put on phantom 1 arbitrarily. Thereby each square of the plate 3 contain no more than one simulator.

It is possible also to make test phantom comprising separate objects which contain test elements.

To estimate characteristics of an information system, the test phantom is put in the place of the research object instead of the object. After obtaining an image of the phantom on the screen of the system, film, or other recording device, the examiner has to choose a group of areas with test elements of certain size or type and to estimate the probability of simulator existence in each area of test phantom image. It is convenient to divide the results of the observation into five groups. The result is 100 if the examiner estimates that the simulator is certainly situated in selected area of the phantom, 75—likely is situated, 50—could either be situated or not, 25—likely is not situated and zero—definitely is absent. Then it is necessary to compare results of answers with the real presence of simulators. The formulas (1)–(3) for calculation of true-positive and true-negative answer, described above can be derived from probability theory. The expression for calculation of true answer probability is obtained from equation $$P = \frac{P(Y/s) + P(N/n)}{P(Y/s) + P(N/s) + P(Y/n) + P(N/n)} = \frac{P(Y/s) + 1 - P(Y/n)}{2}. \quad (4)$$

For practical application of the method it is more comfortable to select l=10, m=5. In this case equations (1)–(3) are simplified:

$$P(Y/s)=2\times 10^{-3}A, \ P(Y/n)=2\times 10^{-3}Z, \ P=10^{-3}(A-Z)+0.5 \quad (5)$$

In order that the examiner will not remember the disposition of test elements, their positions must be change.

Except for the described constructions of test phantoms, other ones can be used having the same set of properties.

By measuring minimum $J_{min.}$ and maximum $J_{max.}$ value of radiation intensity when test elements with pre-established size are distinguished with given probability it is possible to define the latitude range of an information system as value of ratio $J_{max}/J_{min}$ as well as radiation sensitivity $S=1/J_{min}$. The inertness of a system can be defined as maximum speed of movement of test phantom when test elements with pre-established size are distinguished with given probability.

The said method and test phantoms can be used in medical diagnostics, flaw detection, optics, psychophysics, radiolocation and other branches of science and technology for threshold sensitivity evaluation, testing and adjusting information systems, as well as for professional training or testing of specialists.

I claim:

1. Test phantom for information systems divided into several areas, being identified on the output image or informative field of system and united in one or several groups comprising in each of these groups identical test elements which may be displaced through areas within a group, so that their final positions are not known by the examiner but may be determined, while the maximum number of the test elements included in a group is less than the number of said areas, and they are arranged so that none of said areas may contain more than one test element.

2. Test phantom according to claim 1 comprising at least two groups of test elements, each of said groups distinguished by the type of identical elements included therein.

3. Test phantom according to claim 1 wherein areas being identified with special marks or objects disposed in or on the phantom.

4. Test phantom according to claim 1 wherein areas being identified visually from shape of the phantom, test elements' disposition and/or experiment conditions.

5. Test phantom according to claim 1 wherein areas being identified by separate device which takes part in forming the image or informative field of the system.

6. Test phantom according to claim 1 wherein a flat disc with test elements can be revolved relatively to a plate divided into numbered areas executed as concentric rings divided into sectors with radial stripes.

7. Test phantom according to claim 1 wherein each test element is located eccentrically in a separated disc which can be displaced within appropriate group of identified areas independently from other ones.

8. Test phantom according to claim 1 consisting of separate objects including test elements.

9. A method of using test phantom according to claim 1 consisting in obtaining an image of the phantom, choosing a group of areas, estimating the subjective likelihood of the signal's existing from test elements on the informative field of system (in percentage) and the defining probabilities of examiner answer by formulas:

probability of true-positive answer $$P(Y/s) = \frac{A}{100m};$$

probability of false-positive answer $$P(Y/n) = \frac{Z}{100(l-n)};$$

probability of true answer $$P = 0.5 \times \left( \frac{A}{100m} - \frac{Z}{100(l-m)} \right) + 0.5,$$

where l is the common number of test phantom areas in the selected group being identified on the informative field of system, m is the number of test elements in the checked group, A is the sum of the examiner's estimations corresponding to areas with test elements, Z is the remaining sum of the examiner's estimations.

* * * * *